US012765794B2

(12) United States Patent
Bredin et al.

(10) Patent No.: US 12,765,794 B2
(45) Date of Patent: Oct. 20, 2026

(54) ELECTRODE DISCHARGE ON A MEASUREMENT DEVICE

(71) Applicant: Withings, Issy les Moulineaux (FR)

(72) Inventors: Jérôme Bredin, Issy les Moulineaux (FR); Brice Brac De La Perrière, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 167 days.

(21) Appl. No.: 18/673,047

(22) Filed: May 23, 2024

(65) Prior Publication Data

US 2024/0398251 A1 Dec. 5, 2024

(30) Foreign Application Priority Data

May 30, 2023 (EP) .................................... 23176230

(51) Int. Cl.
*A61B 5/0533* (2021.01)
*A61B 5/00* (2006.01)
*A61B 5/308* (2021.01)

(52) U.S. Cl.
CPC ............ *A61B 5/0533* (2013.01); *A61B 5/308* (2021.01); *A61B 5/6829* (2013.01)

(58) Field of Classification Search
CPC ..... A61B 5/0533; A61B 5/308; A61B 5/6829; A61B 5/0537; A61B 5/318; A61B 5/6887; G01G 19/50
See application file for complete search history.

(56) References Cited

U.S. PATENT DOCUMENTS

2008/0015641 A1 1/2008 Armstrong et al.
2014/0257119 A1 9/2014 Lemay
2017/0049352 A1* 2/2017 Mirov .................. A61B 5/6843
2017/0105646 A1 4/2017 Bryenton et al.
2017/0188955 A1* 7/2017 Banet ................... A61B 5/6892
2018/0177459 A1* 6/2018 Eletr .................. A61B 5/14552
2021/0321893 A1* 10/2021 Zhou .................. A61B 5/02438

FOREIGN PATENT DOCUMENTS

CN 110840454 B 3/2021
EP 1 091 215 B1 3/2005
FR 3 131 521 A1 7/2023
WO WO 2006/136598 A2 12/2006
WO WO 2008/107324 A1 9/2008
WO WO 2013/075963 A1 5/2013
WO WO 2014/033105 A1 3/2014
WO WO 2015/036530 A1 3/2015
(Continued)

OTHER PUBLICATIONS

Extended European Search Report as issued in European Patent Application No. 23176230.3, dated Nov. 20, 2023.
(Continued)

*Primary Examiner* — Carl H Layno
*Assistant Examiner* — Maria Catherine Anthony
(74) *Attorney, Agent, or Firm* — CUSHMAN PARTNERS LLC

(57) ABSTRACT

A measurement device and a method associated are presented. The measurement device includes a discharging circuit and a DC measurement circuit connected to electrodes. The discharging circuit is aimed at discharging charges on the electrodes.

21 Claims, 8 Drawing Sheets

(56) References Cited

FOREIGN PATENT DOCUMENTS

| | | |
|---|---|---|
| WO | WO 2016/083432 A1 | 6/2016 |
| WO | WO 2023/126220 A1 | 7/2023 |

OTHER PUBLICATIONS

Rosa, B. M. G., et al., "Smart Wireless Headphone for Cardiovascular and Stress Monitoring," 2017 IEEE 14th International Conference on Wearable and Implantable Body Sensor Networks (BSN), IEEE, May 2017, pp. 75-78, XP033101774.

Xu, J., et al., "A 36 μW 1.1 $mm^2$ Reconfigurable Analog Front-End for Cardiovascular and Respiratory Signals Recording," IEEE Transactions on Biomedical Circuits and Systems, IEEE, vol. 12, No. 4, Aug. 2018, pp. 774-783, XP011688651.

* cited by examiner

ELECTRODE DISCHARGE ON A MEASUREMENT DEVICE

CROSS-REFERENCE TO RELATED APPLICATIONS

This application claims priority to European Patent Application No. EP23176230, filed May 30, 2023, the entire content of which is incorporated herein by reference in its entirety.

FIELD

The present disclosure relates to devices configured to perform physiological measurements of a user body using a direct excitation source (called "DC measurements"), such as an electrochemical skin conductance (ESC) of a user. Such ESC measurements enable to estimate a neurologic state of the user, and for example to detect diabetes. More particularly, the present disclosure relates to such devices that may be used at home, on a regular basis, notably bathroom scales.

For example, documents WO2006/136598, WO2008/107324, WO2013/075963, WO2014/033105, WO2015/036530, WO2016/083432 (called thereafter "SudoScan™ documents") describe a system allowing such an ESC evaluation.

BACKGROUND

Some physical phenomena will be disclosed in relation to the ESC but they similarly apply when a direct excitation source is applied.

The ESC measurement typically includes applying, at a pair of electrodes in contact with the human body (e.g., two feet) a direct voltage at an anode and measuring a voltage at a cathode to determine a current going through the body using a measurement resistor.

In 2022 and 2023, Withings™ launched new body scales called Body Scan™ and Body Comp™, which were able to measure in a single measurement session—i.e. during which the user is standing on the body scale—a weight, an ESC measurement, body impedance (so called BIA, for fat and muscle mass notably), Pulse Wave Velocity (PWV) using a ballistocardiograph (BCG) and an impedance plethysmogram (IPG), and even an electrocardiogram (ECG). To carry out the ESC evaluation and the BIA (and PWV as well), those body scales incorporate electrodes on an upper surface.

SUMMARY

However, because either direct current is injected in the user's feet or because direct voltage potentials are applied to the user's feet with the electrodes, electrochemical reactions occur at the electrodes. The inventors have noticed that the electrodes may remained in an unstable electrochemical state after such measurement. This can deteriorate the quality of the future measurements or alter the value of the future measurements carried out by the same electrode, especially BIA measurements or ECG measurements.

The ESC measurement in particular is responsible for the electrochemical reactions occurring at the electrodes, given that direct current is applied, while alternative current or voltage is used for BIA or IPG.

An aspect of the present invention is aimed at improving the measurement quality and precision, and particularly of the BIA measurements and/or ECG measurements.

The present description relates to a measurement device (notably a body scale) and a method of measurement, wherein one of the measurements uses a source of direct excitation (and not alternative excitation such as an alternative current in BIA), for example the measurement is the electrochemical skin conductance (ESC) of the user's foot or feet.

According to an aspect, the disclosure relates to a measurement device configured to perform a physiological measurement of a user body using a direct excitation source, referred to as a DC measurement, or a physiological measurement of a user body using an alternative excitation source, referred to as an AC measurement, or an ECG (electrocardiogram) measurement. The measurement device may be a body scale. More specifically, the measurement device comprises:

- a pair of electrodes comprising a left electrode and a right electrode configured each to be respectively in contact with the left foot and the right foot of the user;
- a DC measurement circuit comprising a direct excitation source configured to apply a direct voltage or current to the left electrode or the right electrode;
- a discharging circuit, configured to be connected to at least one of the left electrode and right electrode;

wherein the measurement device is configured to:

- discharge at least one of the left electrode and the right electrode using the discharging circuit connected to the at least one of the left electrode and the right electrode;
- perform a DC measurement using the DC measurement circuit connected to the pair of electrodes or perform a ECG measurement using the ECG measurement circuit connected to at least one electrode of the pair of electrodes.

The pair of electrodes is therefore discharged of electric charges so that a same pair of electrodes can carry out a DC measurement and an AC or ECG measurement without deteriorating the latter.

The measurement device typically includes a measurement plate on which the pair of electrodes is placed. In use, the user steps on the measurement plate. When the measurement device is a body scale, the same pair of electrodes is therefore often used to carry out measurements (up to several times a day for a family).

In an implementation, the measurement device is configured to discharge before and/or after performing a DC measurement.

The measurement device may further include an AC measurement circuit comprising an alternative excitation source configured to apply an alternative voltage or current to the left electrode or the right electrode. The measurement device is further configured to perform an AC measurement using the AC measurement circuit connected to at least one electrode of the pair of electrodes (both electrodes in an implementation).

The measurement device may further include an ECG measurement circuit, configured to be connected to at least one electrode of the pair of electrodes. The measurement circuit is further configured to perform an ECG measurement using the ECG measurement circuit connected to at least one electrode of the pair of electrodes.

In an implementation, the measurement device is configured to discharge before and/or after performing an AC or ECG measurement.

In an implementation, the measurement device is configured to perform an AC or ECG measurement after discharging and/or before the DC measurement.

The pair of electrodes may be made of indium tin oxide (ITO).

In an embodiment, the discharging circuit comprises a ground. The ground may be a ground of control circuit (such as a processor of control circuitry).

In an embodiment, the DC measurement circuit further comprises a measurement resistor connected to the ground and configured to determine a current value flowing through the user body, wherein an electrical resistance value (Rm) of the measurement resistor is variable amongst a zero value and predetermined range, wherein the discharging circuit comprises the measurement resistor set to the zero value. The predetermined range may be between 3 kOhms and 500 kOhms.

In an embodiment, the discharging circuit comprises an excitation source, for example the direct excitation source of the DC measurement circuit, wherein the excitation source is set to a zero voltage.

In an embodiment, combining several embodiments disclosed above, the discharging circuit comprises a ground and the direct voltage source.

In an embodiment, the measurement device is configured to perform in the following order: the discharge then the AC measurement and then the DC measurement and then optionally another discharge.

In an embodiment, the measurement device further comprises a commutator configured to selectively connect at least one of the left electrode and the right electrode to:

- the discharging circuit in a set of discharging positions;
- (when applicable) the AC measurement circuit in a set of AC positions;
- (when applicable) the ECG measurement circuit a set of ECG positions; and
- the DC measurement circuit in a set of DC positions, wherein the measurement device is configured to set the commutator in the discharging position to discharge, in the AC position to carry out the AC measurement, in the ECG position to carry out the ECG measurement, and in the DC position to carry out the DC measurement. The commutator typically comprises switches.

The set of discharging positions may include an inversion between the left electrode and the right electrode.

In an embodiment, the measurement device comprises control circuitry configured to control the commutator, the direct excitation source and the alternative excitation source.

In an embodiment, the set of discharging positions are included in the set of DC positions.

In an embodiment, the measurement device includes a weight sensor and is further configured to acquire weight data using the weigh sensor. The measurement device is also configured to discharge at least partially during the acquiring weight data. This allows to shorten the duration of the measurements.

In an embodiment, the measurement device is further configured to associate a user profile of the measurement device to a user standing on the measurement device, where the measurement device is configured to discharge at least partially during identifying (804), wherein associating is performed using weight data. The measurement device includes a measurement plate on which the pair of electrodes is placed. In use, the user steps on the measurement plate.

The weight sensor is configured to measure a load from the measurement plate.

According to another aspect, the disclosure relates to a method to perform a physiological measurement of a user body using a direct excitation source, referred to as a DC measurement. The method may be carried out using a measurement device as disclosed above. The method comprises:

- discharging at least one of the left electrode and the right electrode using the discharging circuit connected to the at least one of the left electrode and the right electrode;
- performing an AC measurement using the AC measurement circuit connected to the pair of electrodes or an ECG measurement using the ECG measurement circuit connected to at least one electrode of the pair of electrode; and
- performing a DC measurement using the DC measurement circuit connected to the pair of electrodes.

More particularly, in an embodiment, the discharging is carried out before and/or after the performing the DC measurement.

More particularly, in an embodiment, the discharging is carried out before and/or after performing the AC measurement.

More particularly, in an embodiment, performing an AC measurement is carried out after discharging and/or before performing the DC measurement.

In an embodiment, discharging is carried out by instructing the commutator to connect at least one of the left electrode and the right electrode to the discharging circuit.

In an embodiment, performing the DC measurement is done by instructing the commutator to connect the pair of electrodes to the DC measurement circuit.

Performing the DC measurement includes instructing the direct excitation source to generate DC excitation.

Discharging may last between 2 and 8 s, even between 5 and 7 s.

In an embodiment, discharging includes:

- connecting one of the left electrode and the right electrode to the ground; and
- connecting the other of the left electrode and the right electrode to the excitation source.

Discharging may further include:

- connecting the one of the left electrode and the right electrode to the direct excitation source, and
- connecting the other of the left electrode and the right electrode to the ground.

In an embodiment, during discharging, the excitation source applies a zero voltage.

In an embodiment, discharging involves selecting the zero value for the electrical resistance value.

In an embodiment, the method further comprises acquiring weight data using the weigh sensor, and discharging is performed at least partially during the acquiring weight data.

Additionally, the method may further comprise identifying a user profile on the measurement device, and discharging is performed at least partially during identifying. For example, identifying is performed using weight data.

According to another aspect, the disclosure also relates to a computer program comprising instructions for control circuitry of a measurement device to carry out a method as defined above. The computer program is stored in a non-transitory machine readable medium.

For all the aspects mentioned above, the DC measurement may be an electrochemical skin conductance, ESC, measurement.

In an embodiment, the ESC measurement comprises:

- applying at least one measurement voltage at the left electrode or right electrode, generating ESC values using at least one voltage measurement at the left electrode and/or the right electrode obtained during the measurement period, wherein a value of the measurement voltage (Va) is variable over time.

In an embodiment, the measurement resistor is connected between the cathode and a reference voltage.

In an embodiment, the predetermined range is between 3 kOhms and 500 kOhms, or between 9.6 kOhms and 300 kOhms. The predetermined range may include a plurality of discrete values, wherein the plurality is comprised between 4 and 32, such as between 4 and 16 and for example 8.

In an embodiment in which the measurement resistor is connected to the cathode, control circuitry measures the voltage value at the cathode.

BRIEF DESCRIPTION OF THE DRAWINGS

These features and benefits of the invention will appear more clearly upon reading the following description, provided solely as a non-limiting example, and done in reference to the appended drawings, in which.

DETAILED DESCRIPTION

General Description of the Measurement Device 100

Figure 1:
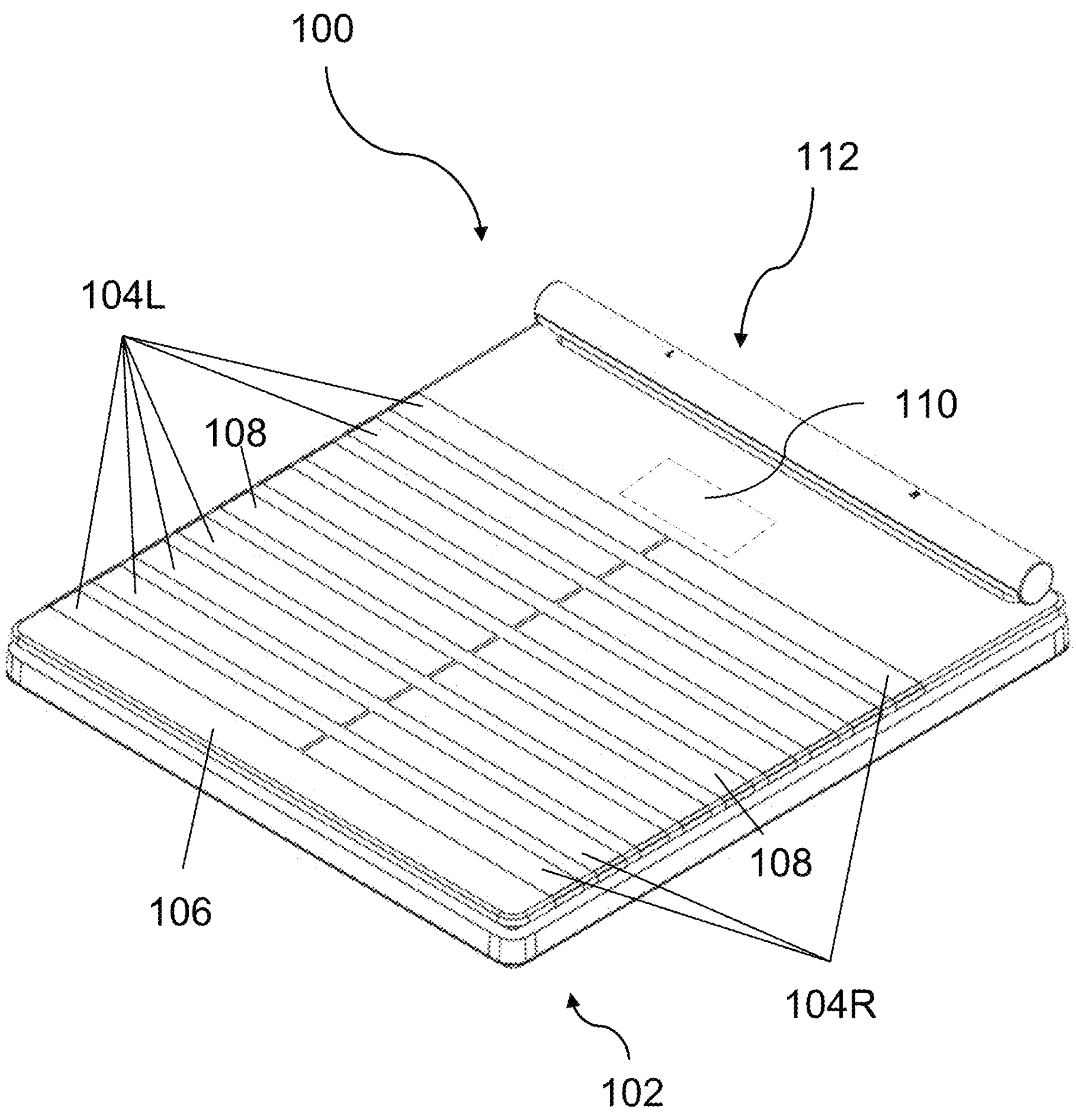
FIG. 1 shows a tridimensional representation of a measurement device according to an embodiment of the disclosure.

FIG. 1 illustrates a measurement device 100 configured to evaluate a physiological measurement of a user body using a direct excitation source (direct current source or direct voltage source). Such measurement will be referred to as a DC measurement. For example, such a DC measurement may be an electrochemical skin conductance, ESC, value of a user. This measurement device 100 is disclosed in further detail in document FR2114739 filed on 31 Dec. 2021. The previously cited SudoScan™ documents disclosed another example of a measurement device. The rest of the description will be exemplified using the ESC measurement but it can be applied to any DC measurement.

The measurement device 100 may also be configured to evaluate a physiological measurement of a user body using an alternative excitation source (alternative current source or alternative voltage source). Such measurement will be referred to as an AC measurement. For example, such an AC measurement may be a body impedance analysis, BIA, or an impedance plethysmogram, IPG. BIA usually includes fat mass and muscle mass. An IPG may be used to compute a pulse wave velocity, PWV.

The measurement device 100 may also be configured to obtain an electrocardiogram, ECG, of the user.

The measurement device 100 comprises a base 102 on which the user may stand with his feet. The base 102 resembles a body scale. As illustrated on FIG. 1, the measurement device 100 may be an electronic bathroom scale, or body scale, or personal scale, on which a user can position himself or herself to notably measure his or her weight. The measurement device 100 is configured to measure weights, for example in the range between 5 kg and 300 kg, in particular within the range between 30 kg and 200 kg. Even if such a device is known as "bathroom scale", it may be used in a bedroom or in another room of a house. In an embodiment, the measurement device 100 may also be configured to measure a body composition, an electrocardiogram (ECG), a Pulse Wave Velocity (PWV), a ballistocardiogram (BCG), etc.

The measurement device 100 includes a pair of electrodes, called the left electrode 104L, and the right electrode 104R, configured to be respectively in contact with the left foot and the right foot of the user. The pair of electrodes 104L, 104R may be located on a measurement plate 106, configured to receive the feet of the user. Therefore, to evaluate an ESC value, in an implementation, all the user needs to do is to stand on the measurement plate 106 and wait for a few seconds to let an ESC evaluation method be performed by the measurement device 100. The same pair of electrodes may be used for a DC measurement, an AC measurement and an ECG measurement (although only one electrode may be used for the ECG measurement).

In a variation, the measurement device 100 may also include at least one additional electrode 108, called reference electrode or HiZ electrode (high impedance electrode). In the example of FIG. 1, all the electrodes on the base 102 includes strips. Some of the strips may be the electrode 104L, 104R, while other strips may be the reference electrode 108. The reference electrode is connected to a high-impedance component, namely a resistor with a high resistance value, so that the current escaping the body through the reference electrode is negligible. More details about this configuration may be found in document FR2114739.

To display information, the base 102 may include a display 110 (e.g., a screen).

Handle 112

In an embodiment, the measurement device 100 may comprise a handle 112, configured to be held by at least one hand of the user. The handle 112 may be connected to the base via a cable (not illustrated) or wireless, via Bluetooth for example. The handle 112 may include the reference electrode (not visible on the drawings). Again, more details about this configuration may be found in FR2114739.

Instead of a handle, a hand device may be used, as disclosed in the SudoScan™ documents.

In a variation, the handle 112 may include the pair of electrodes used for the ESC measurement. The reference electrode 108 may thus be on the base 102.

Electronic Architecture of the Measurement Device 100

Figure 2:
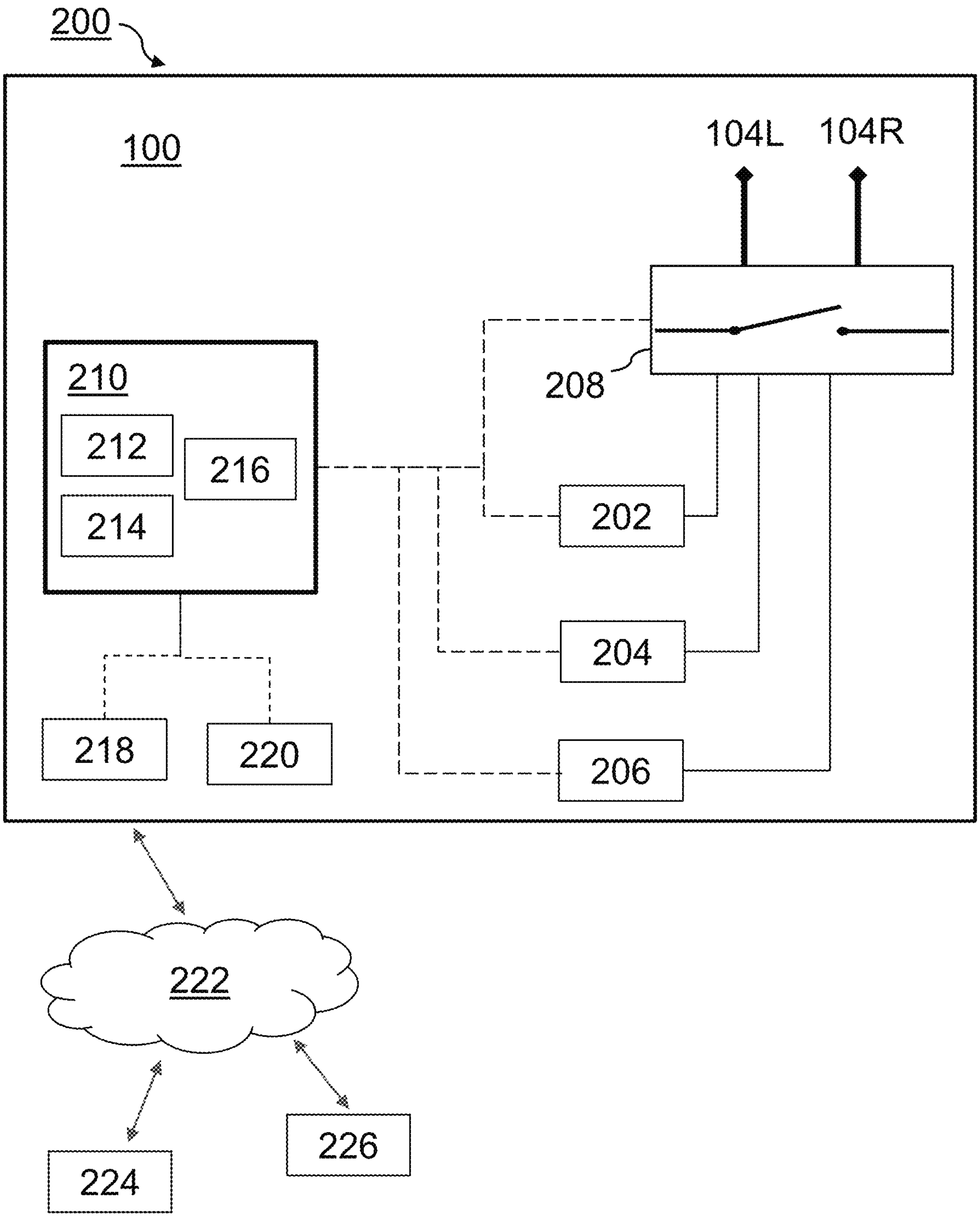
FIG. 2 shows a simplified schematic representation of a measurement device according to an embodiment of the disclosure.

FIG. 2 illustrates a schematic representation 200 of the measurement device 100. The measurement device includes one or more electronic circuits to carry out its functions. In an implementation, the one or more electronic circuits comprise a processor and a non-transitory machine readable medium (e.g. a memory) that stores instructions executable by the processor to perform one or more of the functions described hereinafter.

The measurement device 100 includes a discharging circuit 202. The role of the discharging circuit 202 is to cause the pair of electrodes 104L, 104R to eliminate electric charges that could be stored thereon after previous DC measurements. It will be disclosed in further detail later.

The measurement device 100 also includes a DC measurement circuit 204. The DC measurement circuit 204 is configured to carry out a DC measurement as disclosed previously and in particular an electrochemical skin conductance (ESC) measurement. The DC measurement circuit 204 will be disclosed in further detail later.

The measurement device 100 also includes an AC measurement circuit 206. The AC measurement circuit 206 is configured to carry out an AC measurement as disclosed previously and in particular a BIA or an IPG. The AC measurement circuit 206 will be disclosed in further detail.

The measurement device 100 also includes an ECG (electrocardiogram) measurement circuit (not represented on the drawings). The ECG measurement circuit is configured to carry out an ECG measurement. The ECG measurement circuit may include a reference electrode on the measurement plate and other acquisition electrodes on the handle.

The measurement device 100 includes a commutator 208 to selectively connect or disconnect the pair of electrodes 104L, 104R to the discharging circuit 202. Indeed, the same pair of electrodes 104L, 104R is used for different measurements, such as one or more AC measurements and one or more DC measurements, and also the discharge. However, electronics may differ between AC and DC measurement circuits, the discharge circuit and also ECG measurement circuit. The commutator 208 is also configured to selectively connect or disconnect the pair of electrodes to the DC measurement circuit 204 and/or the AC measurement circuit 206 and/or to selectively connect or disconnect at least one electrode of the pair of electrodes to the ECG measurement circuit.

As it will be observed later on in the description, the discharging circuit 202 may be included in the DC measurement circuit 204. In addition, the commutator 208 includes an open position, in which the electrodes are left floating. The commutator 208 may include switches to create physical connection between electrically conductive material.

The measurement 100 includes a control circuitry 210. Control circuitry 210 may include a processor 212, a memory 214 storing instructions for the processor 212 and an I/O interface 216 to receive and send data. Control circuitry 210 may also include an analog to digital converter (ADC) and a digital to analog converter (DAC). Control circuit 210 is configured to instruct the commutator 208 to selectively connect the pair of electrodes 104L, 104R to the discharging circuit 202, the DC measurement circuit 204, the AC measurement circuit 206 and/or to switch to the open position. Control circuity 210 is further configured to control the DC measurement circuit 204 and/or the AC measurement circuit 206. In an embodiment, control circuitry 210 is further configured to control the discharging circuit 202.

The measurement device 100 may include a weight sensor 218. The weight sensor 218 may include load cells. The weight sensor 218 is configured to send weight data to control circuitry 210 which then is configured to determine a weight of the user based on the weight data. The weight sensor 218 is typically arranged to receive a load from the measurement plate. It may be placed between the measurement plate and a mainframe or feet.

Control circuitry 210 may also be configured to identify a user stepping on the body scale amongst a plurality of registered users. A registered user is a user for which the body scale stores a user profile containing data about the user. For example, such data includes weight data, age data and/or sex data. One way to identify a user is to use weight, for example to compare weight data obtained by the weight sensor 218 with weight data of the stored user profile and determines whether the weight data is to be attributed to the user profile.

The measurement device 100 may further include a wireless module 220 to send and receive data from a communications network 222, which may be hybrid (wireless and/or wired, such as BLUETOOTH® (a short-range wireless technology standard), Wi-Fi, Ethernet, etc.). Those data may be received from or sent to a remote server 224 and/or to a personal mobile phone 226 (e.g., smartphone, tablet, etc.). For example, the DC measurement values may be sent by control circuitry 210 to the server 224, which then forwards those data to the personal mobile phone 226.

Figure 3:
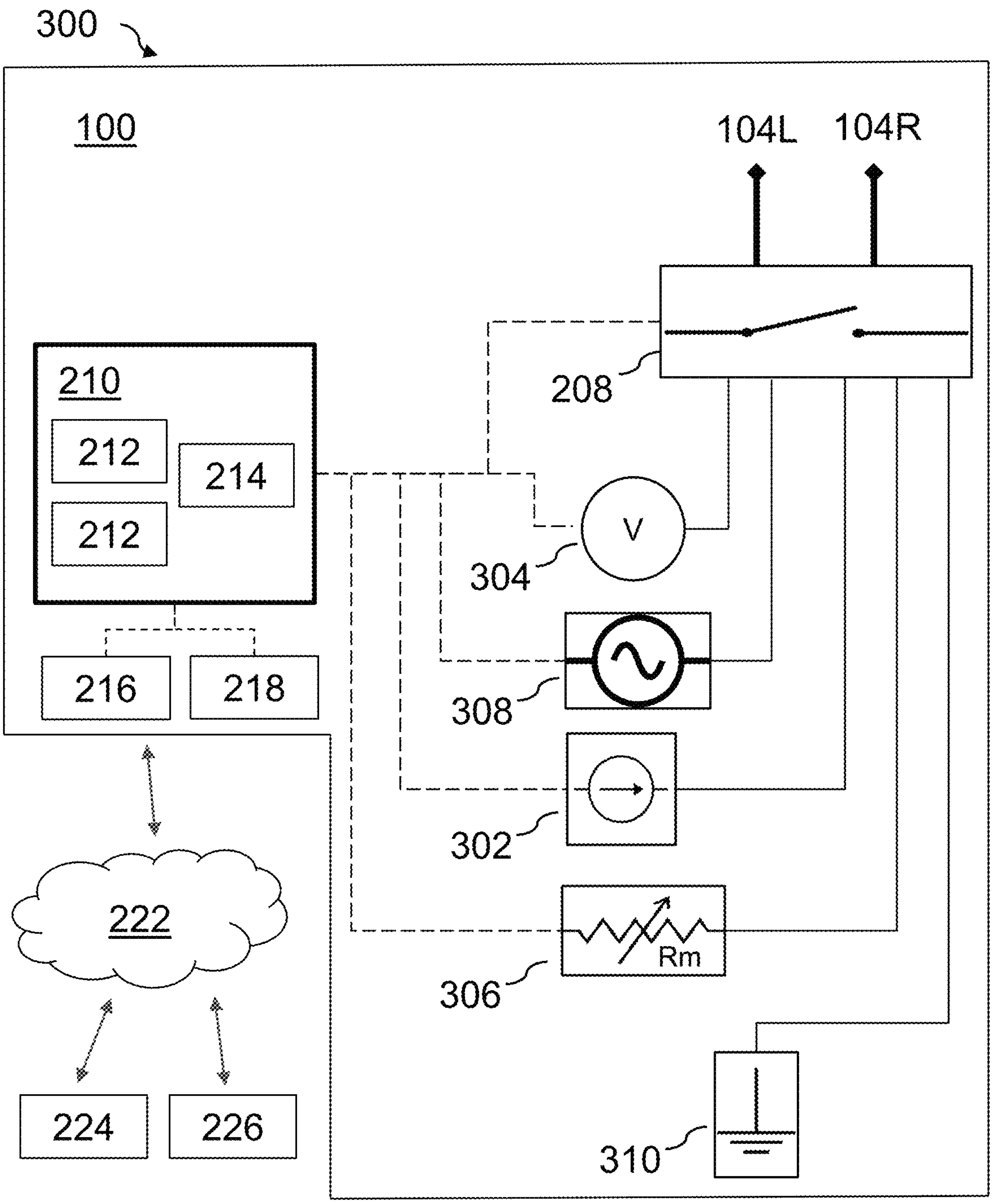
FIG. 3 shows a more detailed schematic representation of an implementation of the measurement device of FIG. 2.
Figure 4:
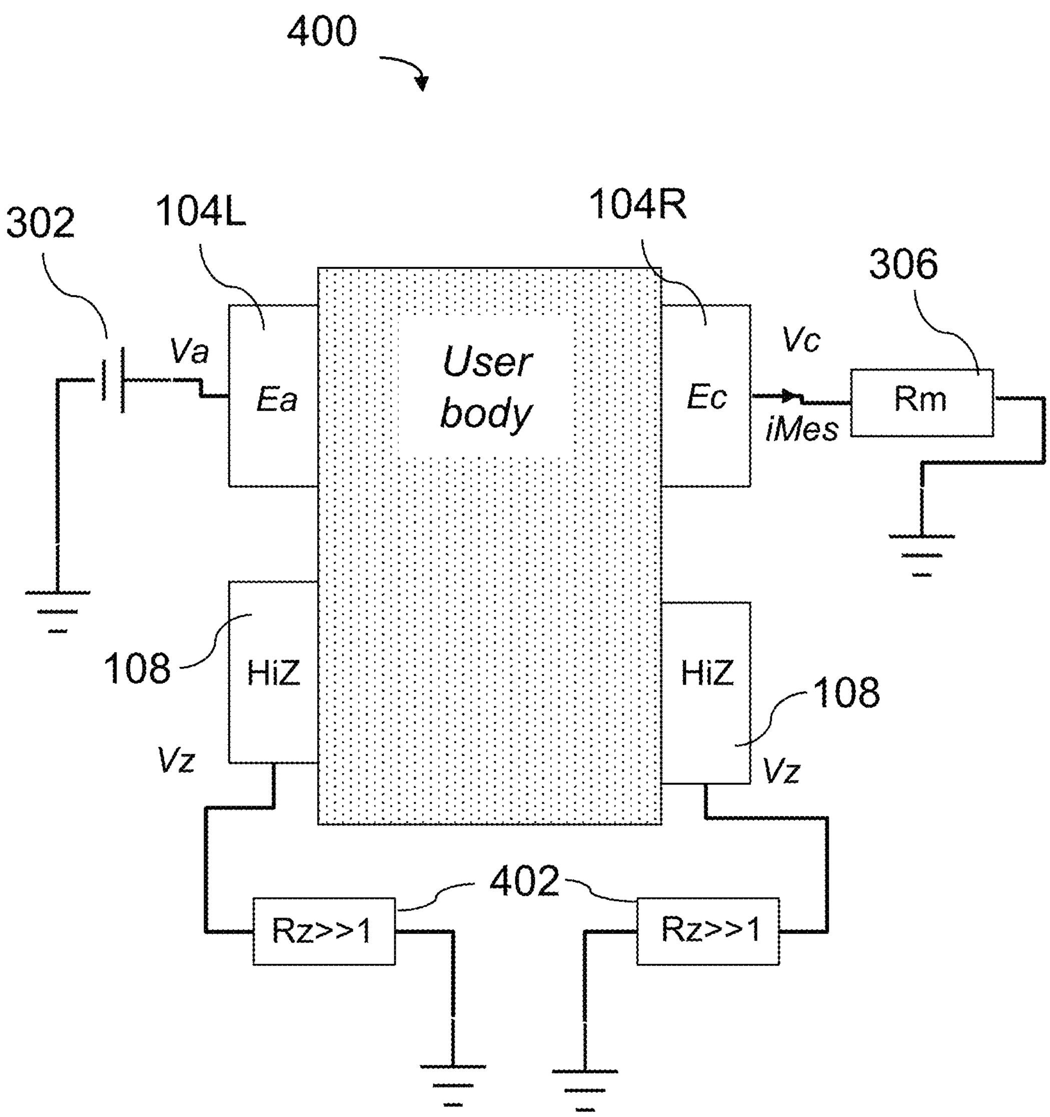
FIG. 4 shows a simplified schematic representation of some components of the measurement device and a user body.

FIG. 3 illustrates a more detailed version 300 of FIG. 2. FIG. 4 illustrates some parts of the measurement device 100 in relation to a user body (e.g., the feet only, the hands only, the feet and the hands).

The DC measurement circuit 202 may comprise a direct excitation source 302, such as a direct voltage source. The direct excitation source 302 may be connected to either one of the electrodes 104L, 104R of the pair of electrodes, which is thus called the anode Ea, through the commutator 208, controlled by control circuitry 210. The other electrode of the electrodes 104L, 104R which is not connected to the direct excitation source 302 is called the cathode Ec. For clarity reasons, in the present description and illustrations, the anode is the "left electrode 104L" and the "right electrode 104R" is the cathode Ec. However, the left electrode 104L may be the cathode Ec and the right electrode 104R may be the anode Ea.

Control circuitry 210 is configured to control the direct excitation source 302, that is to say to send a voltage instruction to the direct excitation source 302. For example, the voltage instruction may be for a constant direct voltage or for a series of decreasing steps. Voltage at the anode Ea is referred to as Va. This voltage usually corresponds to the instructed voltage to the direct excitation source 302.

The DC measurement circuit 204 may also comprise a voltage sensor 304, configured to measure a voltage value. Voltage measured at the cathode Ec is referred to as Vc.

The commutator 208 allows to change the electrical connection of the electrodes by switching some electrical connections between the electrodes 104L, 104R and other elements, and in particular the direct excitation source 202. In a particular implementation, the commutator 208 may be configured to invert the anode Ea and the cathode Ec on the pair of electrodes 104L, 104R. The commutator 208 may have further functions, as presented in document FR2114739, for bioimpedance analysis for example. In a detailed embodiment of the description, the commutator 208 has at least the following positions: an open position (electrodes 104L, 104R are left floating), a set of AC positions (in which the electrodes 104L, 104R are connected to the AC measurement circuit 206), a set of DC positions (in which the electrodes 104L, 104R are connected to the DC measurement circuit 204). Other positions, such as ECG (electrocardiogram) positions are needed when the measurement device 100 is configured to perform an ECG. The set of AC positions may include several positions, depending on the AC measurement to be carried out (several BIAs, IPG, etc.). Document PCT/EP2022/086492 shows some examples. The set of DC positions may include a left DC position in which the left electrode 104L is connected to the DC excitation source 302 (usually called anode) and a right DC position in which the right electrode 104R is connected to the DC excitation source 302.

When the discharging circuit 202 is not included in the DC measurement circuit 204, the commutator 208 has also a set of discharging positions (in which the electrodes are connected to the discharging circuit 202). This set includes at least one position.

Measurement Resistance

When the DC measurement is an ESC measurement, the DC measurement circuit 204 also includes a measurement resistor 306 configured to compute a current value flowing through the body. In an embodiment, the measurement resistor 306 is connected between a reference voltage and one electrode of the pair of electrodes 104L, 104R, e.g., that which is not connected to the direct excitation source 302, i.e. the cathode Ec. The commutator 208 may be used to switch the connection between on the one hand the measurement resistor 306 and on the other hand the left electrode 104L or the right electrode 104R so as to switch from an anode/cathode configuration to a cathode/anode configuration.

The reference voltage may be a ground voltage of a ground of the measurement device 100.

Other configurations are possible, as long as a voltage difference around the measurement resistance 306 may be determined and a voltage difference relative to the user body may be determined.

The measurement resistor 306 has an electrical resistance value Rm known from control circuitry 210. The electrical resistance value Rm is variable among a predetermined range and may be changed by control circuitry 210. In an implementation, the predetermined range goes from 3 kOhms to 500 kOhms or even between 9.6 kOhms and 300 kOhms. The measurement resistor 306 may include an array of resistors connected together with switches, so that to the predetermined range is constituted by a plurality of discrete values. The switches may be operated by control circuitry 210. In an implementation, the plurality is comprised between 4 and 32, even between 4 and 16, and may be 8. Using a voltage value of the cathode Ec, called Vc, and the electrical resistance value Rm, control circuitry 210 may determine a current iMes flowing through the user body. Conversely, as the reference electrode 108 is high impedance, the current therein is negligible, therefore generating no loss.

In an embodiment that will be described later, the electrical resistance value Rm is variable among the predetermined range and zero. In other words, the measurement resistor 306 becomes equivalent to a wire when the value Rm is set to zero.

The AC measurement circuit 206 includes an alternative excitation source 308 configured to generate an alternative current or voltage at the electrodes 104L, 104R. The alternative excitation source 308 may be used for bioimpedance such as BIA, for bioimpedance analysis—fat mass, water, bone, etc. or such as impedance plethysmography, IPG, etc.), as described in detail in document FR2114739. The alternative excitation source 308 may be an alternative current source.

In a similar manner to the direct excitation source 302, the electrodes are connected to the alternative excitation source 308 through the commutator 208.

To steer the alternative current to the appropriate electrodes and to measure a voltage value at the appropriate electrodes, the commutator 208 is activated by control circuitry 210.

In the present description, "excitation source" shall mean the direct excitation source or the alternative excitation source.

Discharging Circuit

Several variations of the discharging circuit 202 will be disclosed.

Ground Passive Discharging Circuit

In an embodiment, referred to as a ground passive discharging circuit, the discharging circuit 202 includes at least one ground 310, which may be the same ground as that of the measurement resistance 306. The ground 310 causes the electrical charges to get or lose electrons to become electronically inactive. When the pair of electrodes 104L, 104R is connected to the discharging circuit 202, the left electrode 104L and the right electrode 104R are both connected to the ground 310 or to two different grounds. The ground 310 is designed to be at a potential of 0V. Ground 310 may be a ground of control circuitry 210 (for example a ground of the processor 212).

As the measurement device 100 works on battery, the ground 310 may be a signal ground and not an earth ground. The ground 310 may be that of control circuitry 210. The ground is a reference point for the whole electronic components linked to the ground 204. It carries a potential of 0V. At least one of the left electrode 104L and the right electrode 104R may be connected to the ground 310 though the commutator 208. The ground mentioned in relation to the resistance measurement and the ground 310 may be the same physical ground.

In an implementation, by connected to the ground 310, it is meant directly connected to the ground 310, with no impedance therebetween (only wires or near-zero impedance elements), as they would hinder the evacuation of the electrical charges.

In an embodiment, the discharging circuit 202 with the ground 310 is a dedicated circuit, which is not included in the DC measurement circuit 204. As disclosed before, the commutator 208 therefore has a set of dedicated discharging positions.

In an embodiment, to connect the electrodes to the ground 310 without adding new connections to the electronic architecture, in particular without complexifying the commutator 208, a solution (called "bypass embodiment") is to set the resistance value Rm of the measurement resistor 306 to the zero value. This way, to connect the electrodes to the ground 310, control circuitry 210 may instruct the measurement resistor 306 to set the resistance value Rm to zero so that the measurement resistor 306 becomes a wire; the position of the commutator 208 is therefore one of the set of DC positions.

Resistance Passive Discharging Circuit

In an embodiment, referred to as a resistance passive discharging circuit, the discharging circuit 202 includes the measurement resistor 306 set to the lowest value of the predetermined range and the ground 310 of the measurement resistance 306.

This solution is not as efficient as the bypass solution as there is a resistor between the electrode and the ground. To connect the electrodes to measurement resistor 306, control circuitry 210 may instruct the measurement resistor 306 to set the resistance value Rm to the lowest value of the predetermined range; the position of the commutator 208 is therefore one of the set of DC positions.

Active Discharging Circuit

In another embodiment (which can be combined with the previous one), referred to as an active discharging circuit, the discharging circuit 202 includes an excitation source, such as the direct excitation source 302 or the alternative excitation source 308, set at a zero voltage. When the pair of electrodes 104L, 104R is connected to the discharging circuit 202, the left electrode 104L and the right electrode 104R are both connected to one of the direct excitation source 302 and the alternative excitation source 308, or are both connected to one of them, with a voltage set by control circuity 210 close to zero or being equal to zero. The use of a low or zero voltage causes the electrical charges to get or lose electrons to become electronically inactive.

Hybrid Discharging Circuit

In another embodiment, referred to as a hybrid discharging circuit, the discharging circuit 202 combines the active discharging circuit and the ground passive discharging circuit or resistance passive discharging circuit. For example (with a ground passive discharging circuit), the hybrid discharging circuit includes the ground 310 and at least one of the direct excitation source 302 and the alternative excitation source 308. In one specific example, the discharging circuit 202 includes the ground 310 and one excitation source, such as the direct excitation source 302. When the pair of electrodes 104L, 104R is connected to the discharging circuit 202, one of the left electrode 104L and the right electrode 104R is connected to the ground and the other of the left electrode 104L and the right electrode 104R is connected to one of the direct excitation source 302 and the alternative excitation source 308 with a voltage set by control circuity 210 close to zero or being equal to zero. The hybrid discharging circuit 202 may include two configurations, typically enabled by the commutators 208 and therefore forms two positions of the sets of DC positions: one position in which the left electrode 104L is connected to the ground 310 and the right electrode 104R is connected to excitation source and one in which the left electrode 104L is connected to the excitation source and the right electrode 104R is connected to the ground 310. The connection to the ground 310 may be carried out using the bypass embodiment disclosed above. Here, the position(s) of the commutator 208 is (are) therefore one(s) of the sets of DC positions.

For example (with a resistance passive discharging circuit), the hybrid discharging circuit includes the same as above except that the ground 310 is replaced by both the measurement resistor 308 at the lowest value of the predetermined range and the ground 310 of the measurement resistor 308.

Materials of the Electrode

The electrodes 104L, 104R may be made of stainless steel, titanium, brass, nickel or an alloy thereof, or even conductive plastics. In one specific embodiment, the electrodes 104L, 104R are made of indium tin oxide, known as ITO. ITO has different properties from stainless steel which favors electro-chemical reactions.

The electrodes 104L, 104R may be a coating on the measurement plate 106.

In an embodiment, the coating is made of ITO and the measurement plate 106 is made of glass.

How to Obtain an ESC Value

More details may be found in the SudoScan™ documents but the general principle will be described here below. As mentioned previously, in the following description, the left electrode 104L is the anode Ea and the right electrode 104R is the cathode Ec. However, thanks to the commutator 208, the left electrode 104L may be the cathode Ec and the right electrode 104R may be the anode Ea.

FIG. 4 illustrates a simplified representation 400 of a user on the measurement system. The user is represented in dots as the "user body". The left foot (or hand) may be in contact with the left electrode 104L which is the anode Ea, connected to the direct excitation source 302. The right foot (or hand) may be in contact with the right electrode 104R which is the cathode Ec, connected to the measurement resistor 306. Each foot (or hand) may also be connected to a reference electrode 108, which is the HiZ electrode, whose impedance is high thanks to one or more resistors 402. A measurement device without the reference electrodes 108 is also possible.

Figure 5:
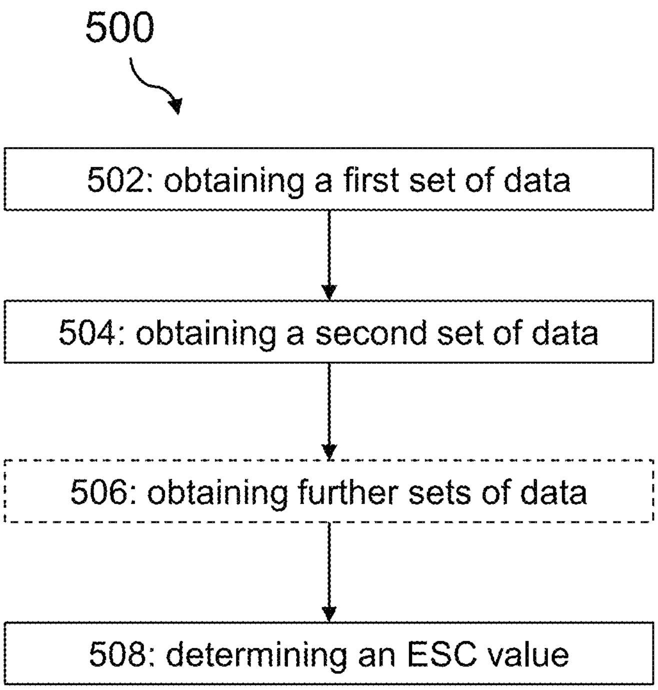
FIG. 5 shows a measurement method to obtain ESC values.

FIG. 5 illustrates a measurement method 500 to measure an ESC value, performed during a measurement period. In addition, a calibration method of the electrical resistance value Rm of the measurement resistor 306 may be performed before the measurement period.

The calibration is aimed at setting the electrical resistance value Rm at an appropriate value, called calibration value Rcalib for acceptability ranges of the electronic components of control circuitry 210. Rm is chosen amongst the predetermined range.

Control circuity 210, at 502, applies a first measurement voltage Va1 at the anode Ea using the direct excitation source 302 and obtain a first measured voltage Vc1 at the cathode Ec, using the voltage sensor 304.

Control circuitry 210 may, at 504, in similar manner to 502, apply a second measurement voltage Va2 at the anode Ea and obtain a second measured voltage Vc2 at the cathode Ec. The second measurement voltage Va2 is different from the first measurement voltage Va1. Steps 502 and 504 are distinct and usually follow each other.

The applied voltages Va at the anode Ea may be comprised between 0 and 5V, for example between 1V and 4V.

With the information of the measured voltage Vc and the electrical resistance value Rm, control circuitry 204 may determine a measured current value iMes flowing through the user body. Therefore using data of step 402 and 404, control circuitry 204 may obtain two sets of data: (Va1; Vc1; iMes1) and (Va2; Vc2; iMes2).

Other measured voltage may be used, as long as a voltage difference in the body user may be obtained and a voltage difference around the resistor may be determined. For example, instead of Va, control circuitry 204 may obtain Vc or Vz (Vz being the voltage value of the HiZ electrode) and instead of Vc, control circuitry 210 may obtain Va or Vz. In this implementation, as the measurement resistor 306 is connected to the anode, Vc is needed to determine the current flowing through the measurement resistor 306.

Control circuitry 210 may generate, at 506, further sets of data using different voltages values (dashed lines on FIG. 4). For example, one additional set of data is generated.

Control circuitry 210 determines, at 508, an ESC value, using the sets of data of 402 and 404 (and 406 if applicable).

More specifically, determining the ESC value may be broken down as follows. Control circuitry 210, may compute a voltage difference using any two of Va, Vc, Vz (Vz being the voltage value of the HiZ electrode) and may determine a linear regression between at least two points comprising each said voltage difference and the associated measurement current value iMes. As illustrated on FIG. 5, control circuitry 210 computes ΔV1=Va1−Vz and ΔV2=Va2-Vz and determines the slope of the linear regression linreg between (ΔV1; iMes1) and (ΔV2; iMes2) (and other points, if any). The slope is representative of the ESC value of the user. To get more precise results, more than two points may be used for the linear regression, as illustrated on FIG. 6. However, only the last few sets of data may be used to determine the ESC value (e.g., the last three).

Figure 6:
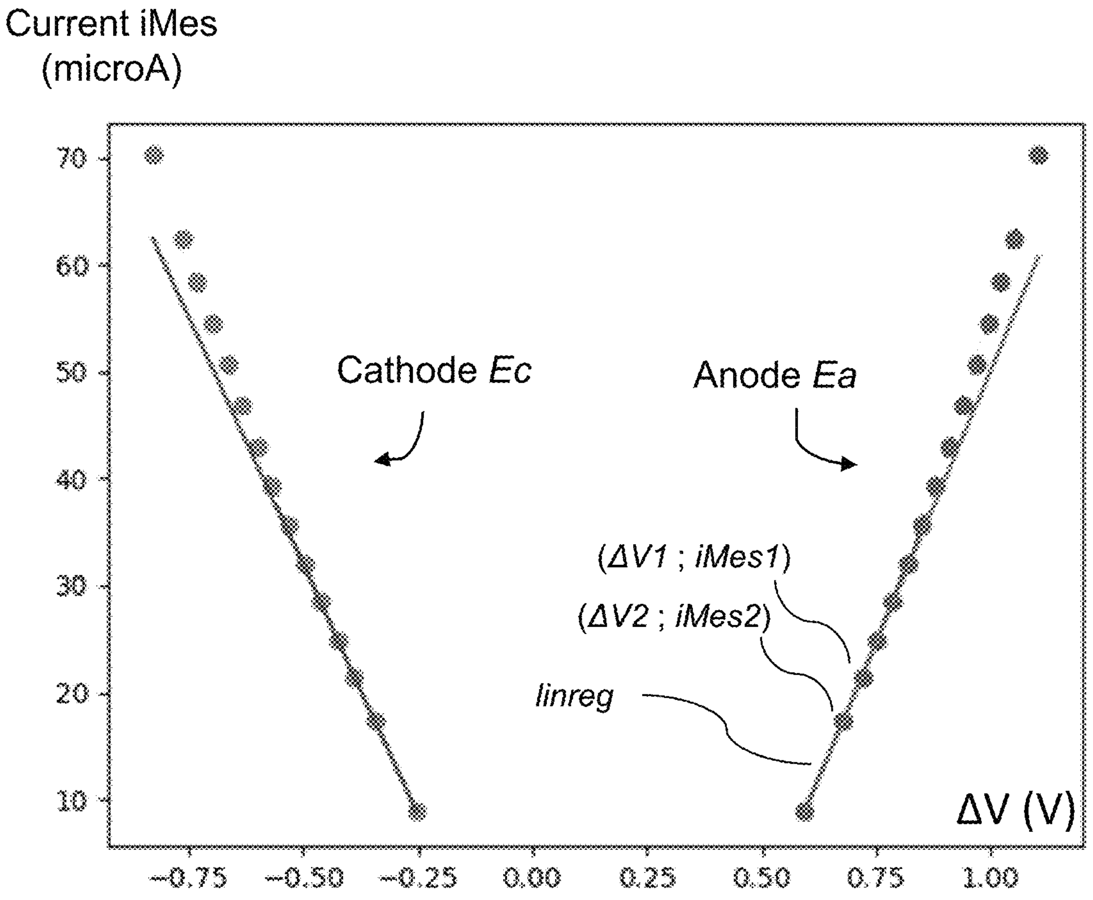
FIG. 6 shows a graph illustrating how ESC values may be determined.
Figure 7:
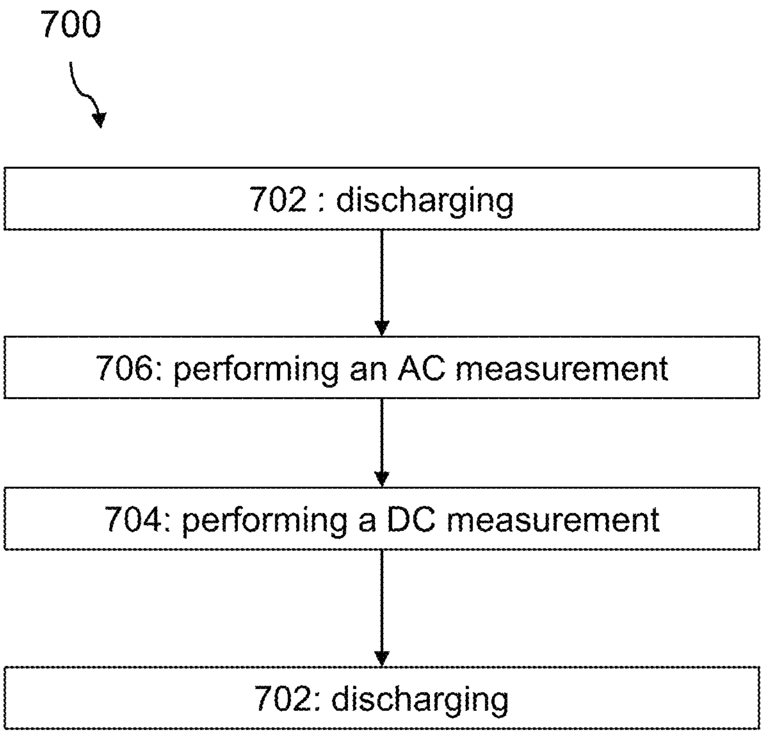
FIG. 7 shows a DC measurement method including a discharging method.

Measurement method 500 may be carried a second time with an anode-cathode inversion, to build the second curve on FIG. 6 and the average of the slope may be carried out. The inversion is typically carried out using the commutator 208, with the left DC position and the right DC position.

In particular, Va-Vz allows to have the ESC value of one foot (the left foot here is contacting the anode Ea), while Vc-Vz allows to have the ESC value of the other foot (the right foot here is contacting the cathode C).

Control circuitry 210 may compute averages of those ESC values to output a single ESC value.

A similar approach may be carried out without Vz, using Va1 and Va2, such that no high-Z electrode 108 is needed.

For example, control circuitry 210 may apply direct voltage steps of decreasing value. Each step may last between 300 ms and 5 s, such as between 300 ms and 700 ms to reduce the length of the ESC measurement. In particular, this reduced duration is permitted by the pre-stabilization method that will be disclosed later.

Measurement Method 700

As it may be observed from the measurement method 500, a direct voltage is applied to the electrodes 104 L, 104R at some point. This may lead to the stacking of electrical charges at the electrodes 104 L, 104R. The goal of the discharge is to reduce the influence of previous DC measurements on other measurements involving the electrodes. As mentioned in the introduction, ESC measurements are generated using direct voltage and displacements of charges between the electrodes and the user's body (feet), notably through sweat generated upon stimulation of the sudoral glands by direct voltage. However, the sweat remaining on the electrodes may be electrically charged and such charges may alter the other measurements.

A method 700 to perform a physiological measurement with a discharge will be described now. Method 700 comprises, regardless of the order, discharging 702 at least one of the pair of electrodes 104 L, 104R (although desirably both) and carrying out a DC measurement 704. In an implementation, discharging 702 is performed before carrying out the DC measurement 704, so that the pair of electrodes is discharged before the DC measurement. In another implementation, discharging 702 is performed after carrying out the DC measurement 704, so that the pair of electrodes 104 L, 104R is put back into its former state, and is therefore ready for a new DC measurement 704 the next time the user steps on the scale. In another implementation, to maximize the performance of the measurement device 100, discharging 702 is performed before and after carrying out the DC measurement 704.

Before discharging 702, the commutator 208 may be in the open position, that is to say the pair of electrodes 104 L, 104R may be left floating.

Carrying out an AC measurement 706 comprises control circuitry 210 to instruct the commutator 208 to connect the pair of electrodes 104L, 104R to the AC measurement circuit 206 and to instruct the alternative excitation source 308 to generate AC excitation. For example, AC measurement 706 may include BIA or IPG (to compute PWV for example).

Carrying out a DC measurement 704 comprises control circuitry 210 to instruct the commutator 208 to connect the electrodes 104L, 104R (or at least one) to the DC measurement circuit 204 and to instruct the direction excitation source 302 to generate a DC excitation. The commutator 208 may be therefore in the left DC position or the right DC position.

Discharging 702 comprises control circuitry 210 to instruct the commutator 208 to a position of the set of discharging positions, that is to say to connect the electrodes 104L, 104R (or at least one) to the discharging circuit 202. When the discharging circuit 202 is a ground passive discharging circuit, the electrical charges will naturally be neutralized thanks to the ground 310 that sets a zero potential to the electrodes 104 L, 104R. In the bypass embodiment, control circuitry 210 sets the resistance value of the measurement resistor 306 to zero. When the discharging circuit is the resistance passive discharging circuit, the electrical charges will naturally be neutralized, but at a slower rate thanks to the ground 310 and the measurement resistor 306. In the embodiment, control circuitry 210 sets the resistance value of the measurement resistor 306 to the lowest value of the predetermined range.

Conversely, when the discharging circuit 202 is an active or hybrid discharging circuit, discharge 702 further comprises control circuitry 210 to instruct the excitation source 302 to set a low or zero voltage. In one particular embodiment, control circuitry 210 instructs the direct excitation source 302 to set a zero voltage.

In an embodiment, with the hybrid discharging circuit 202, discharging 702 may further include inverting between the left/right configuration to the right/left configuration, so that each of the left electrode 104L and right electrode 104R is successively connected to the ground 310 and the excitation source 302 set at a low or zero voltage. This ensures a better symmetry in the discharging process. For example, such inversion can be done by switching between the right DC position and the left DC position, in the embodiment in which the discharging circuit is included in the DC measurement circuit.

The presence of electric charges on the electrodes also alters AC measurement. Therefore, in an embodiment, method 700 further includes, before or after discharging 702, carrying out an AC measurement 706. In an embodiment, discharging 702 is performed before, to discharge the electrodes for the AC measurement. To optimize the duration of the measurement method 700, AC measurement 706 is carried out before the DC measurement 704, to avoid having to discharge the electrodes before the AC measurement 706.

Discharging 702 may last between 2 s and 8 s, even between 5 s and 7 s.

Discharging 702 takes some time. However, the user must spend as little time as possible on the measurement device. To improve to measurement flow, the discharging may be carried out during the weighing and/or identification steps of the measurement device.

Figure 8:
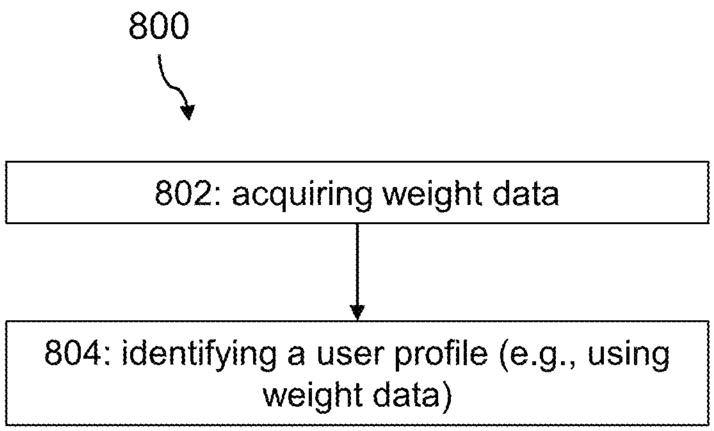
FIG. 8 shows a flowchart directed to an acquisition of weight data.

More precisely, as illustrated on flow 800 of FIG. 8, method 700 may further comprise acquiring weight data 802 by control circuit 210 using the weigh sensor. Acquiring weight data 802 may last between 1 s and 4 s. Discharging 702 may be carried out during acquiring weight data 802, or at least partially during, so that the overall duration of the measurement sequence is not increased or only slightly increased.

Based on weight data, method 700 may further comprise identifying 804 a user profile stored in the measurement device 100. Discharging 702 may be carried out during identifying 804, or at least partially during.

In those embodiments, discharging 702 is performed at least before performing a DC measurement.

The embodiment of identifying 804 may be carried out using other data than weight data (impedance data, proximity sensor, Bluetooth detection, etc.).

The method presented here also applies whenever there is a need to discharge electrodes on a body scale. Therefore, the measurement may be any type of measurement using a direct source of excitation, such as a direct voltage source used for the ESC measurement or a direct source of current.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

It will be appreciated that the various embodiments and aspects of the inventions described previously are combinable according to any technically permissible combinations. For example, various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The present invention has been described and illustrated in the present detailed description and in the figures of the appended drawings, in possible embodiments. The present invention is not however limited to the embodiments described. Other alternatives and embodiments may be deduced and implemented by those skilled in the art on reading the present description and the appended drawings.

In the claims, the term "includes" or "comprises" does not exclude other elements or other steps. The different characteristics described and/or claimed may be beneficially combined. Their presence in the description or in the different dependent claims do not exclude this possibility. The reference signs cannot be understood as limiting the scope of the invention.

The invention claimed is:

1. A measurement device configured to perform physiological measurements of a user body using a direct excitation source, referred to as a DC measurement, or using an alternative excitation source, referred to as an AC measurement, the measurement device comprising:

a pair of electrodes comprising a left electrode and a right electrode configured to be respectively in contact with the left foot and the right foot of the user;

a measurement plate configured to receive the user and on which the pair of electrodes is placed;

a DC measurement circuit comprising a direct excitation source configured to apply a direct voltage or current to the left electrode or the right electrode;

an AC measurement circuit comprising an alternative excitation source configured to apply an alternative voltage or current to the left electrode and/or the right electrode;

a discharging circuit, configured to be connected to at least one of the left electrode and right electrode, and a commutator configured to selectively connect at least one of the left electrode and the right electrode to:

the discharging circuit in a set of discharging positions; and the DC measurement circuit in a set of DC positions, wherein the measurement device is configured to:

set the commutator a discharging position to discharge at least one of the left electrode and the right electrode using the discharging circuit connected to the at least one of the left electrode and the right electrode;

perform the AC measurement using the AC measurement circuit connected to at least one electrode of the pair of electrodes; and set the commutator in a DC position to perform the DC measurement using the DC measurement circuit connected to the pair of electrodes.

2. The measurement device according to claim 1, wherein the discharging circuit comprises a ground.

3. The measurement device according to claim 2, wherein the DC measurement circuit further comprises a measurement resistor connected to the ground and configured to determine a current value flowing through the user body, wherein an electrical resistance value of the measurement resistor is variable amongst a zero value and predetermined range, wherein the discharging circuit comprises the measurement resistor set to the zero value.

4. The measurement device according to claim 1, wherein the discharging circuit comprises an excitation source set to a zero voltage.

5. The measurement device according to claim 4, wherein the discharging circuit is a direct excitation source of the DC measurement circuit.

6. The measurement device according to claim 1, which is configured to perform the discharge, then the AC measurement and then the DC measurement and then optionally another discharge.

7. The measurement device according to claim 1, further configured to discharge before performing the AC measurement.

8. The measurement device according to claim 1, further configured to discharge after performing the DC measurement.

9. The measurement device according to claim 1, further configured to perform the AC measurement before the DC measurement.

10. The measurement device according to claim 1, further comprising a weight sensor and further configured to acquire weight data using the weight sensor, wherein the measurement device is configured to discharge at least partially during acquisition of the weight data.

11. The measurement device according to claim 1, further configured to associate a user profile of the measurement device to a user standing on the measurement device, where the measurement device is configured to discharge at least partially during identifying the user.

12. The measurement device according to claim 1, wherein the set of discharging positions of the commutator includes a first discharging position in which the left electrode is connected to the discharging circuit and a second discharging position in which the right electrode is connected to the discharging circuit, the measurement device being configured to set the commutator successively in the first and second discharging positions during discharging.

13. The measurement device according to claim 1, wherein the commutator further comprises an open position in which the left electrode and the right electrode are left floating, and wherein the measurement device is configured to set the commutator in the open position before setting the commutator in a discharging position.

14. A method to perform a physiological measurement of a user body using a direct excitation source, referred to as a DC measurement, wherein the method is carried out using the measurement device according to claim 1, wherein the method comprises:

discharging at least one of the left electrode and the right electrode using the discharging circuit connected to the at least one of the left electrode and the right electrode;

performing the AC measurement using the AC measurement circuit connected to the pair of electrodes; and performing the DC measurement using the DC measurement circuit connected to the pair of electrodes.

15. The method according to claim 14, wherein the discharging is performed before performing the AC measurement.

16. A non-transitory machine readable medium comprising instructions configured to carry out the method of claim 14.

17. A measurement device configured to perform physiological measurements of a user body using a direct excitation source, referred to as a DC measurement, or to perform an electrocardiogram, ECG, measurement, the measurement device comprising:

a pair of electrodes comprising a left electrode and a right electrode configured each to be respectively in contact with the left foot and the right foot of the user;

a measurement plate configured to receive the user and on which the pair of electrodes is placed;

a DC measurement circuit comprising a direct excitation source configured to apply a direct voltage or current to the left electrode or the right electrode;

an ECG measurement circuit configured to obtain an electrocardiogram of the user using at least one electrode of the pair of electrode;

a discharging circuit, configured to be connected to at least one of the left electrode and right electrode, and a commutator configured to selectively connect at least one of the left electrode and the right electrode to:

the discharging circuit in a set of discharging positions; and the DC measurement circuit in a set of DC positions, wherein the measurement device is configured to:

set the commutator in a discharging position to discharge at least one of the left electrode and the right electrode using the discharging circuit connected to the at least one of the left electrode and the right electrode;

perform the ECG measurement using the ECG measurement circuit connected to at least one electrode of the pair of electrodes; and set the commutator in a DC position to perform the DC measurement using the DC measurement circuit connected to the pair of electrodes.

18. The measurement device according to claim 17, further configured to discharge before performing the ECG measurement.

19. A method to perform a physiological measurement of a user body using a direct excitation source, referred to as a DC measurement, wherein the method is carried out using a measurement device of claim 17, wherein the method comprises:

discharging at least one of the left electrode and the right electrode using the discharging circuit connected to the at least one of the left electrode and the right electrode;

performing an ECG measurement using the ECG measurement circuit connected to at least one electrode of the pair of electrodes; and performing a DC measurement using the DC measurement circuit connected to the pair of electrodes.

20. The method according to claim 19, wherein the discharging is performed before performing the ECG measurement.

21. A non-transitory machine readable medium comprising instructions configured to carry out the method of claim 19.

* * * * *